(12) United States Patent
Wu et al.

(10) Patent No.: US 12,144,580 B2
(45) Date of Patent: Nov. 19, 2024

(54) SYSTEM AND METHOD FOR MANAGING BLUETOOTH LOW ENERGY ADVERTISING

(71) Applicant: Pacesetter, Inc., Sylmar, CA (US)

(72) Inventors: Yongjian Wu, Saratoga, CA (US); Chao-Wen Young, Cupertino, CA (US); Jun Yang, Valencia, CA (US); Reza Shahandeh, Tarzana, CA (US); Gabriel A. Mouchawar, Valencia, CA (US)

(73) Assignee: Pacesetter, Inc., Sylmar (CA)

( * ) Notice: Subject to any disclaimer, the term of this patent is extended or adjusted under 35 U.S.C. 154(b) by 278 days.

(21) Appl. No.: 17/712,544

(22) Filed: Apr. 4, 2022

(65) Prior Publication Data
US 2022/0225879 A1 Jul. 21, 2022

Related U.S. Application Data

(63) Continuation of application No. 16/934,592, filed on Jul. 21, 2020, now Pat. No. 11,317,803.

(51) Int. Cl.
*A61N 1/372* (2006.01)
*A61B 5/00* (2006.01)
(Continued)

(52) U.S. Cl.
CPC ............ *A61B 5/002* (2013.01); *A61B 5/0031* (2013.01); *A61B 5/686* (2013.01);
(Continued)

(58) Field of Classification Search
None
See application file for complete search history.

(56) References Cited

U.S. PATENT DOCUMENTS

| 6,141,774 A | 10/2000 | Mattheis |
| 7,672,722 B1 | 3/2010 | Mengotto |
| (Continued) | | |

FOREIGN PATENT DOCUMENTS

| EP | 2636426 A1 | 9/2013 |
| WO | 2016143973 A1 | 9/2016 |
| WO | 2019126101 A1 | 6/2019 |

OTHER PUBLICATIONS

European Search Report for related European Patent Application No. 21170259.2 dated Oct. 15, 2021 (5 pages).

*Primary Examiner* — Tuan A Tran
(74) *Attorney, Agent, or Firm* — Dean D. Small; The Small Patent Law Group, LLC

(57) ABSTRACT

Computer implemented methods and systems are provided that comprise, under control of one or more processors of a medical device, where the one or more processors are configured with specific executable instructions. The methods and systems include sensing circuitry configured to define a sensing channel to collect biological signals, memory configured to store program instructions, a processor configured to implement the program instructions to at least one of analyze the biological signals, manage storage of the biological signals or deliver a therapy, and communication circuitry configured to wirelessly communicate with at least one other implantable or external device, the communication circuitry configured to transition between a sleep state, a partial awake state and a fully awake state. When in the fully awake state, the communication circuitry is configured to execute tasks and actions associated with a communications protocol startup (CPS) instruction set that includes an advertisement scanning related (ASR) instruction subset and a non-ASR instruction subset. When in the partially awake state, the communication circuitry is configured to execute, as the ASR instruction subset, transmit (Continued)

advertising notices over one or more channels according to a wireless communications protocol, scan the one or more channels for a connection request from an external device. When a connection request is not received, return to the sleep state, without performing actions or tasks associated with the non-ASR instruction subset of the CPA instruction set.

18 Claims, 6 Drawing Sheets

(51) Int. Cl.
    *G06F 12/02* (2006.01)
    *H04B 1/40* (2015.01)
    *H04W 4/80* (2018.01)
    *H04W 48/16* (2009.01)
    *H04W 52/02* (2009.01)
    *H04W 76/10* (2018.01)
    *A61B 5/145* (2006.01)
    *A61N 1/37* (2006.01)
    *A61N 1/375* (2006.01)
    *A61N 1/39* (2006.01)

(52) U.S. Cl.
    CPC .......... *G06F 12/0238* (2013.01); *H04W 4/80* (2018.02); *H04W 48/16* (2013.01); *H04W 76/10* (2018.02); *A61B 5/14503* (2013.01); *A61B 2560/0209* (2013.01); *A61N 1/3702* (2013.01); *A61N 1/37211* (2013.01); *A61N 1/3756* (2013.01); *A61N 1/3956* (2013.01)

(56) References Cited

U.S. PATENT DOCUMENTS

| | | |
|---|---|---|
| 8,145,279 B2 | 3/2012 | Kim et al. |
| 8,488,506 B2 | 7/2013 | Husted et al. |
| 8,544,106 B2 | 9/2013 | Haider et al. |
| 9,634,496 B2 | 4/2017 | Elad et al. |
| 9,678,763 B2 | 6/2017 | Park |
| 9,681,381 B2 | 6/2017 | Kang |
| 9,687,658 B2 * | 6/2017 | Wu .................. A61N 1/37223 |
| 9,853,969 B2 * | 12/2017 | Enke .................. H04W 4/80 |
| 9,855,433 B2 * | 1/2018 | Shahandeh ........ A61N 1/37252 |
| 9,907,150 B2 | 2/2018 | Roquemore, III |
| 9,992,439 B2 | 6/2018 | Lee et al. |
| 10,045,296 B2 | 8/2018 | Vasishtha et al. |
| 10,124,176 B2 | 11/2018 | Wu et al. |
| 10,182,336 B1 | 1/2019 | Stockton et al. |
| 10,313,860 B2 | 6/2019 | Montemurro et al. |
| 10,390,225 B2 | 8/2019 | Mao |
| 10,397,869 B2 * | 8/2019 | Zacchio ............... H04W 88/06 |
| 10,449,372 B2 | 10/2019 | Wu et al. |
| 10,543,370 B2 | 1/2020 | Doudna et al. |
| 10,552,614 B2 | 2/2020 | Nguyen et al. |
| 10,617,875 B2 * | 4/2020 | Demmer .............. A61N 1/3727 |
| 10,834,563 B2 | 11/2020 | Lo |
| 10,863,432 B2 | 12/2020 | Densbergen et al. |
| 11,007,370 B2 * | 5/2021 | Shahandeh ........ A61N 1/37217 |
| 11,018,071 B2 | 5/2021 | Pinkham |
| 11,032,686 B2 | 6/2021 | Montemurro et al. |
| 11,065,457 B2 * | 7/2021 | Wang .................. A61N 1/37276 |
| 11,243,595 B2 | 2/2022 | Cheng et al. |
| 11,290,954 B2 * | 3/2022 | Li ........................ H04W 52/028 |
| 11,337,151 B2 * | 5/2022 | Shaw .................... H04W 76/11 |
| 11,452,881 B2 * | 9/2022 | Sturman ................ G16H 40/63 |
| 11,534,618 B2 * | 12/2022 | Sturman ................. H04W 4/06 |
| 2010/0014140 A1 | 1/2010 | Akedo et al. |
| 2014/0206346 A1 | 7/2014 | Kiukkonen et al. |
| 2015/0065047 A1 | 3/2015 | Wu et al. |
| 2015/0319674 A1 | 11/2015 | Hughes et al. |
| 2015/0382304 A1 | 12/2015 | Park |
| 2018/0078777 A1 | 3/2018 | Wu et al. |
| 2018/0088646 A1 | 3/2018 | Chen et al. |
| 2018/0184380 A1 | 6/2018 | Xue |
| 2019/0036886 A1 | 1/2019 | Wu et al. |
| 2019/0114393 A1 | 4/2019 | Andersen |
| 2020/0128482 A1 | 4/2020 | Daoura et al. |
| 2020/0375455 A1 | 12/2020 | Tassel et al. |

* cited by examiner

SYSTEM AND METHOD FOR MANAGING BLUETOOTH LOW ENERGY ADVERTISING

REFERENCE TO RELATED APPLICATIONS

The present application is a continuation application of, and claims priority to, U.S. application Ser. No. 16/934,592, Titled "SYSTEM AND METHOD FOR MANAGING BLUETOOTH LOW ENERGY ADVERTISING" which was filed on 21 Jul. 2020, the complete subject matter of which is expressly incorporated herein by reference in its entirety.

BACKGROUND

An implantable medical device (IMD) is a medical device that is configured to be implanted within a patient anatomy and commonly employs one or more leads with electrodes that either receive or deliver voltage, current or other electromagnetic pulses from or to an organ or tissue for diagnostic or therapeutic purposes. In general, IMDs include a battery, electronic circuitry, a pulse generator, a transceiver and/or a microprocessor that is configured to handle communication with an external instrument as well as control patient therapy. The components of the IMD are hermetically sealed within a metal housing.

IMDs are generally programmed by, and exchange data with, external instruments controlled by physicians and/or the patient. Some commercially available external instruments use commercial operating systems (e.g., iOS, Android) that communicate through wireless bi-directional communication links with the IMDs. For example, mobile devices with Bluetooth Low Energy (BLE) circuitry are available for communication with certain implantable medical devices. The bi-direction communication links are formed using a wireless communication protocol that includes advertisement notices received by the external instruments. The advertisement notices are broadcast by the IMD at predetermined constant frequencies. The use of the advertising notices to facilitate the establishment of wireless communications involves a significant power consumption for the implanted medical device.

Currently, during an advertising operation, a BLE enabled IMD transmits advertise notices and searches for scan requests from external devices. Often the IMD is in a sleep state when it is time to perform an advertising operation. Thus, the IMD must first wake up from the sleep state before the IMD is able to transmit an advertisement notice and searches for a scan request. Each time the IMD awakes from the sleep state, the IMD performs a predetermined set of startup and initialization actions or tasks. The IMD utilizes a certain amount of power to perform all of the startup and initialization actions/task associated with waking up. Over the life of an IMD, the IMD will go to sleep and awake from the sleep state a substantially large number of times (e.g., several times each day for several years). Consequently, the actions and tasks that are performed during every wake-up operation, just to perform an advertising operation, utilize an unduly large amount of power over the life of the device.

A need remains for an improved manner to manage the advertising operations of an IMD.

BRIEF SUMMARY

In accordance with an embodiment herein, an implantable medical device (IMD) is provided, including sensing circuitry configured to collect biological signals, memory configured to store program instructions and a processor configured to implement the program instructions to analyze the biological signals and/or manage storage of the biological signals or deliver a therapy. The IMD further includes communication circuitry configured to wirelessly communicate with at least one other implantable or external device. The communication circuitry may be configured to transition between a sleep state, a partial awake state and a fully awake state. When in the fully awake state, the communication circuitry may be configured to execute tasks and actions associated with a communications protocol startup (CPS) instruction set that includes an advertisement scanning related (ASR) instruction subset and a non-ASR instruction subset. When in the partially awake state, the communication circuitry may be configured to execute functions, as the ASR instruction subset. The functions may include to transmit advertising notices over one or more channels according to a wireless communications protocol and to scan the one or more channels for a connection request from an external device. When a connection request is not received, the communication circuitry may return to the sleep state without performing actions or tasks associated with the non-ASR instruction subset of the CPS instruction set.

In another aspect, a computer implemented method is provided. Under control of one or more processors of a medical device, where the one or more processors are configured with specific executable instructions, the method may include collecting biological signals, and implementing program instructions to analyze the biological signals and/or manage storage of the biological signals and/or deliver a therapy. The method may also include communicating wirelessly with at least one other implantable or external device and executing tasks and actions associated with a communications protocol startup (CPS) instruction set that includes an advertisement scanning related (ASR) instruction subset and a non-ASR instruction subset when in the fully awake state. When in a partially awake state, the method may include executing functions, as the ASR instruction subset. The functions may include transmitting advertising notices over one or more channels according to a wireless communications protocol, scanning the one or more channels for a connection request from an external device, and returning to a sleep state, without performing actions or tasks associated with the non-ASR instruction subset of the CPS instruction set when a connection request is not received.

In another aspect, a computer program product is provided. The computer program product may include a non-signal computer readable storage medium with computer executable code to collect biological signals. The computer program product may also include computer executable code to analyze the biological signals, and/or manage storage of the biological signals, and/or deliver a therapy. The computer program product may also include computer executable code to communicate wirelessly with at least one other implantable or external device and execute tasks and actions associated with a communications protocol startup (CPS) instruction set that includes an advertisement scanning related (ASR) instruction subset and a non-ASR instruction subset when in the fully awake state. When in a partially awake state, the computer executable code may execute functions, as the ASR instruction subset. The functions may include to transmit advertising notices over one or more channels according to a wireless communications protocol, scan the one or more channels for a connection request from an external device, and return to a sleep state without performing actions or tasks associated with the non-ASR instruction subset of the CPS instruction set when a connection request is not received.

DETAILED DESCRIPTION

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes and/or by electrodes positioned within or proximate to the heart wall and/or chambers of the heart.

The terms "body generated analyte" and "BGA" shall mean a test substance or specimen that is naturally generated by or naturally present in a human body as defined in U.S. Provisional Patent Application 62/875,870, titled "METHODS, DEVICE AND SYSTEMS FOR HOLISTIC INTEGRATED HEALTHCARE PATIENT MANAGEMENT", filed Jul. 18, 2019, the complete subject matter of which is incorporated herein by reference.

The term "BGA test device" shall mean any and all equipment, devices, disposable products utilized to collect and analyze a BGA as defined in the '870 provisional application. The BGA test device may implement one or more of the methods, devices and systems described in the '870 provisional application.

The term "biological signal" shall include CA signals, BGA data indicative of a BGA and the like.

The term "low power" refers to an amount of power that is utilized by the IMD over a series of predefined actions or tasks that occur upon entry into a partially awake state.

The term "high power" refers to an amount of power that is utilized by the IMD over a series of predefined actions or tasks that occur upon entry into a fully awake state.

The terms "low power" and "high power" are used in a relational manner with respect to one another and are not used to denote specific power levels.

Figure 1A:
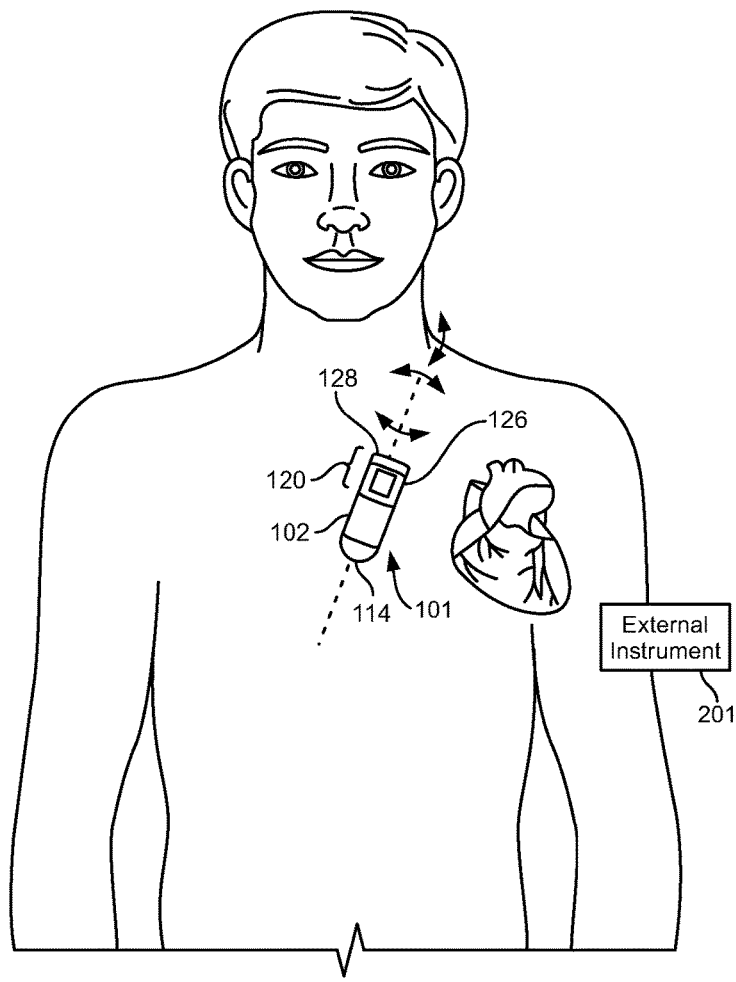
FIG. 1A illustrates a graphical representation of a heart with an implantable medical device (IMD) implemented in accordance with embodiments herein.

FIG. 1A illustrates an implantable medical device (IMD) 101 intended for subcutaneous implantation at a site near the heart. The IMD 101 includes a pair of spaced-apart sense electrodes 114, 126 positioned with respect to a housing 102. The sense electrodes 114, 126 provide for detection of far field electrogram signals. Numerous configurations of electrode arrangements are possible. For example, the electrode 114 may be located on a distal end of the IMD 101, while the electrode 126 is located on a proximal side of the IMD 101. Additionally or alternatively, electrodes 126 may be located on opposite sides of the IMD 101, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 102 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external instrument 201 in accordance with one or more predetermined wireless protocols (e.g., Bluetooth, Bluetooth low energy, Wi-Fi, etc.).

The housing 102 includes various other components such as: sense electronics for receiving signals from the electrodes, a microprocessor for analyzing the far field CA signals, including assessing the presence of R-waves in cardiac beats occurring while the IMD is in different locations relative to gravitational force, a loop memory for temporary storage of CA data, a device memory for long-term storage of CA data, sensors for detecting patient activity, including an accelerometer for detecting acceleration signatures indicative of heart sound, and a battery for powering components.

In at least some embodiments, the IMD 101 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor-tissue interface. The IMD 101 may be configured to be activated by the patient or automatically activated, in connection with recording subcutaneous ECG signals. The IMD 101 senses far field, subcutaneous CA signals, processes the CA signals to detect arrhythmias and if an arrhythmia is detected, automatically records the CA signals in memory for subsequent transmission to an external instrument 201.

As explained herein, the IMD 101 includes electrodes that collect cardiac activity (CA) signals in connection with multiple cardiac beats and in connection with different IMD locations (e.g., different positions and/or different orientations). The IMD 101 also includes one or more sensors to collect acceleration signatures that are indicative of heart sounds produced at different points in a cardiac cycle.

Figure 1B:
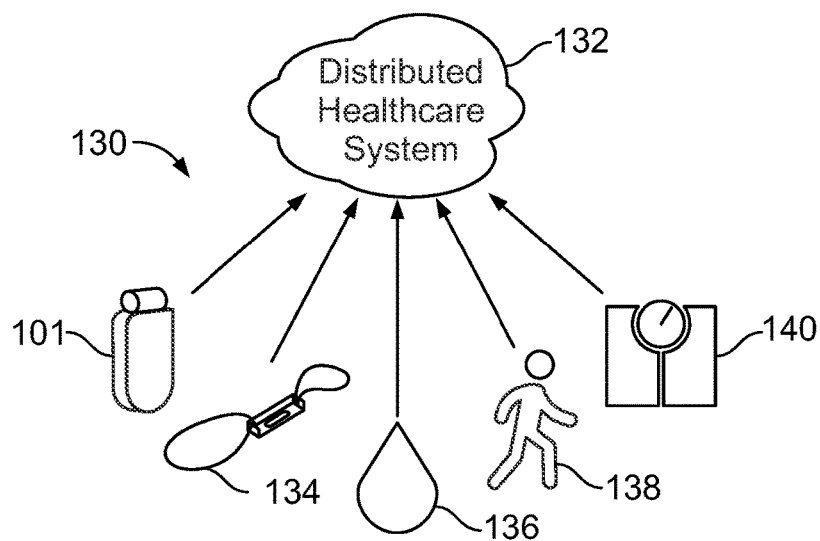
FIG. 1B illustrates a system for integrating external diagnostics with remote monitoring provided by implantable medical devices that manage waking-up the communications circuitry in accordance with embodiments herein.

FIG. 1B illustrates a system for integrating external diagnostics with remote monitoring provided by implantable medical devices that manage waking-up the communications circuitry in accordance with embodiments herein. The system may be implemented with various architectures, that are collectively referred to as a healthcare system 132. By way of example, the healthcare system 132 may be implemented as described herein. The healthcare system 132 is configured to receive data from a variety of external and implantable sources including, but not limited to, active IMDs 101 capable of delivering therapy to a patient, passive IMDs or sensors 134, BGA test devices 136, wearable sensors 138, and point-of-care (POC) devices 140 (e.g., at home or at a medical facility). A POC device 140 may represent one type of BGA test device 136. The data from one or more of the external and/or implantable sources is collected and transmitted to one or more secure databases within the healthcare system 132.

For example, the external BGA test device 136 may collect lab test results for specific tests and then transmit the lab test results to the healthcare system 132. The BGA test device 136 may be implemented at a variety of physical locations, such as one or more "core" laboratories, a physician's office, ER (emergency room), OR (operating room) and/or a medical facility POC (e.g., during hospitalizations or routine healthcare visits). The BGA test device 136 may be implemented as an at-home POC device 140 that collects test results periodically or continuously monitor one or more body generated analytes (e.g., blood glucose). The at home POC device may include mobile devices such as iPhone, Android phone, or other mobile device that has Bluetooth wireless network such as Wi-Fi or cellular data capabilities. The at home POC device 140 may transmit the raw BGA data to the medical network (e.g., a local external device and/or remote server). Additionally or alternatively, the at-home POC device 140 may implement a corresponding test of the BGA data for a characteristic of interest (COI) such as a malnutrition state COI, an electrolyte COI, a cardiac marker COI, a hematology COI, a blood gas COI, a coagulation COI, an endocrinology COI. The POC device 140 transmits the COI (and optionally the BGA data) to the healthcare system 120 as the tests are performed at home or elsewhere. The POC device 140 may implement periodic or continuous tests for glucose levels, such as through sensors and handheld devices offered under the trademark FREESTYLE LIBRE® by Abbott Laboratories. Optionally, the BGA test device 136 may be implemented as a fully implantable "lab on a chip", such as an implantable biosensor array, that is configured to collect lab test results.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. The IMD may represent or include a BGA test device as described in the '870 provisional application. The IMD may represent a cardiac monitoring device, pacemaker, cardioverter, cardiac rhythm management device, defibrillator, neurostimulator, leadless monitoring device, leadless pacemaker, and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may be a leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference. Additionally or alternatively, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein. Additionally or alternatively, the IMD may be a leadless cardiac monitor (ICM) that includes one or more structural and/or functional aspects of the device(s) described in U.S. patent application having Docket No. A15E1059, U.S. patent application Ser. No. 15/084,373, filed Mar. 29, 2016, entitled, "METHOD AND SYSTEM TO DISCRIMINATE RHYTHM PATTERNS IN CARDIAC ACTIVITY," which is expressly incorporated herein by reference.

All references, including publications, patent applications and patents, cited herein are hereby incorporated by reference to the same extent as if each reference were individually and specifically indicated to be incorporated by reference and were set forth in its entirety herein.

Figure 2:
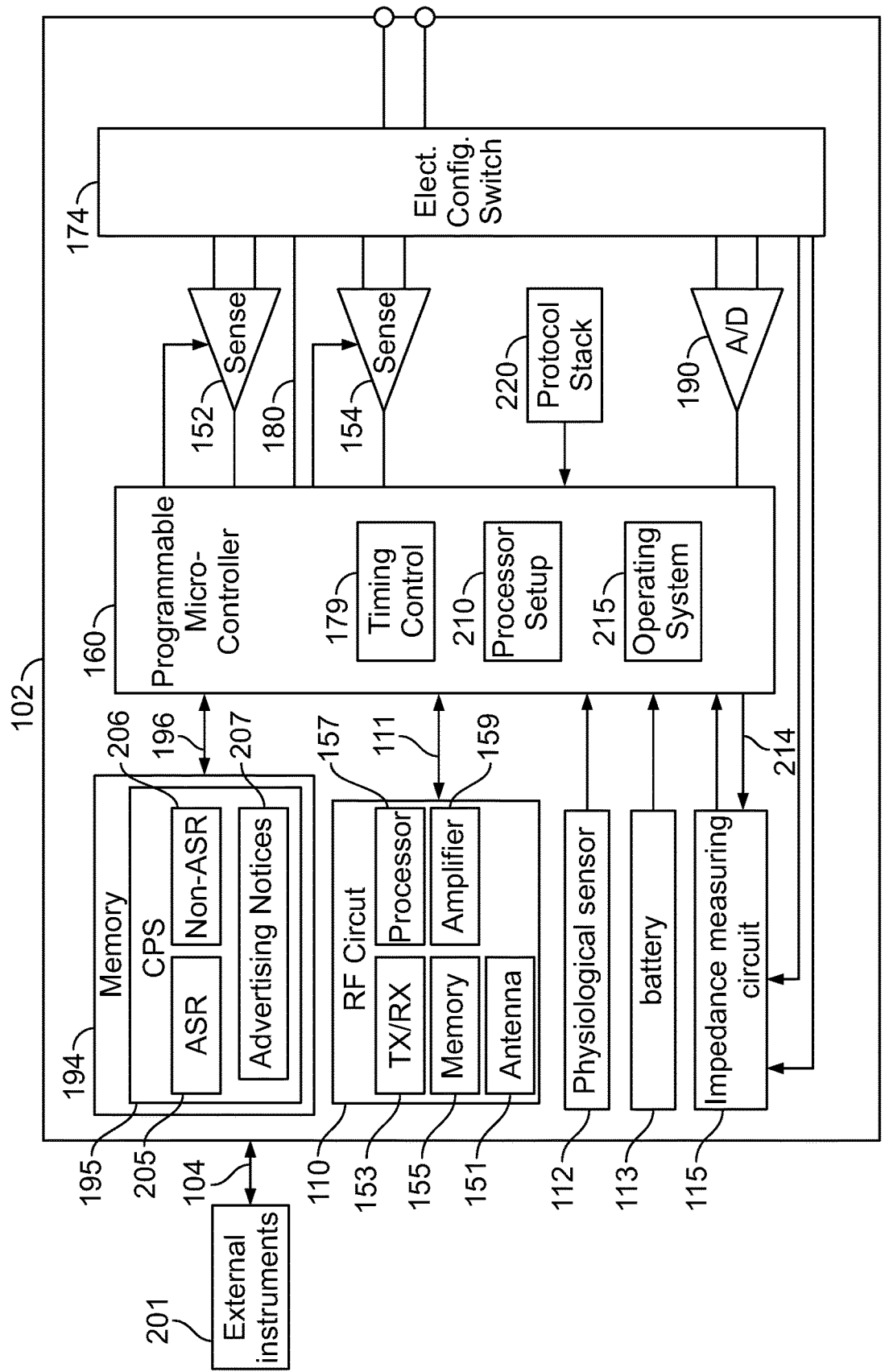
FIG. 2 illustrates a block diagram of an IMD formed in accordance with embodiments herein.

FIG. 2 illustrates a block diagram of internal components of the IMD 101. The components described herein can include or represent hardware and software instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. Additionally or alternatively, the components may be hard-wired logic circuits.

The IMD 101 is for illustration purposes only, and it is understood that the circuitry could be duplicated, eliminated or disabled in any desired combination to provide a device capable of treating the appropriate heart chamber(s) with cardioversion, defibrillation and/or pacing stimulation as well as providing for apnea detection and therapy. Additionally or alternatively, the IMD 101 may be used to generate neurostimulation for application to a desired area of a body, such as spinal cord stimulation, the brain and the like. The housing 102 for the IMD 101, shown schematically in FIG. 2, is often referred to as the "can", "case" or "case electrode" and may be programmably selected to act as the return electrode for all "unipolar" modes. The housing 102 may further be used as a return electrode alone or in combination with one or more of the coil electrodes for shocking purposes. The housing 102 further includes a connector (not shown) having a plurality of terminals. In other embodiments, such as when the IMD represents a transvenous device, the terminals may be configured to be coupled to different types of electrodes and leads. All or a portion of the terminals may be used in various combinations. The IMD 101 includes a controller circuit 160 which controls operation of the IMD 101. The controller circuit 160 may include one or more processors that are configured to implement program instructions, stored in memory, to at least one of analyze the biological signals, manage storage of the biological signals or deliver a therapy. The controller circuit 160 (also referred to herein as a processor module or unit) may include one or more processors, or equivalent control circuitry, designed specifically for controlling the monitoring, analysis, storage and transmission of CA signals, device markers, arrhythmias and the like.

The controller circuit 160 is configured to communicate with various RAM or ROM memory, logic and timing circuitry, state machine circuitry, and I/O circuitry. Typically, the controller circuit 160 includes the ability to process or monitor input signals (data) as controlled by program code stored in memory. The details of the design and operation of the controller circuit 160 are not critical to this disclosure. Rather, any suitable controller circuit 160 may be used that carries out the functions described herein. Among other things, the controller circuit 160 receives, processes, and manages storage of digitized cardiac data sets from the various sensors and electrodes. For example, while the current IMD 101 as shown may not collect and analyze cardiac data sets such as IEGM data, additionally or alternatively, the IMD 101 may collect, analyze and wireless transmit pressure data, heart sound data, and the like.

The controller circuit 160 further includes timing control circuitry 179 used, among other things, to wake the IMD 101 from a sleep state. The timing circuitry 179 may include a clock for synchronizing the timing of advertising/connection events and for entering a sleep state between the advertising/connection events. The clock may determine when the IMD 101 should wake up next after processing the advertising/connection events before going to sleep. The timing circuitry 179 may then set an event to wake up in time for the next advertising/connection events. Additionally, the controller circuit 160 may include a startup module 210. The processor startup module may include program instructions saved in ROM that, when executed, are utilized to control modules within the IMD 101, such as the memory 194, RF circuit 110, and the like. Alternatively, the startup module 210 may be located on another circuit other than the controller circuit within the IMD 101. The controller circuit 160 includes an operating system module 215. The operating system module 215 supports the applications that run within the IMD 101. Alternatively, the operating system module 215 may be located on a circuit other than the controller circuit 120. Alternatively, the protocol stack 220 may be located on another circuit other than the controller circuit within the IMD 101. The protocol stack may include a controller and a host, each containing various communication layers.

A sensing circuit 182 and sensing circuit 184 may also be selectively coupled to one or more leads through the switch 174 for collecting sensed physiologic data (e.g., cardiac activity, neural activity, respiratory activity, etc.). The sensing circuits, 182 and 184, may include dedicated sense amplifiers, multiplexed amplifiers or shared amplifiers. The outputs of the sensing circuits, 182 and 184, are connected to the controller circuit 160 which, in turn, receives the sensed data and is able to trigger or inhibit the pulse generators, 170 and 172, respectively, in a demand fashion in response to the absence or presence of activity of interest.

Sensed signals are also applied to the inputs of an analog-to-digital (ND) data acquisition system 190. The data acquisition system 190 is configured to acquire IEGM signals, neural signals, and the like. The data acquisition system 190 converts the raw analog data into a digital signal and stores the digital signals in memory 194 for later processing and/or RF transmission to the EI 201. The data acquisition system 190 is coupled to one or more leads through the switch 174 to sample signals across any combination of desired electrodes. The data acquisition system 190 may also be coupled, through switch 174, to one or more of the acoustic sensors. The data acquisition system 190 acquires, performs A/D conversion, produces and saves the digital pressure data, and/or acoustic data.

The RF circuit 110 includes communication circuitry, such as an antenna 151, a transceiver 153, memory 155, a processor 157 and a collection of one or more transmit amplifiers and receive amplifiers (shown collectively as amplifiers 159). For example, the processor 157 may be similar to the microcontroller 160. Optionally, the transceiver 151 may be provided as a single component or a separate transmitter and a separate receiver. The one or more transmit amplifiers 159 are configured to be selectively connected between an output of the transmitter of the transceiver 153 and the antenna 151. The one or more receive amplifiers 159 are configured to be selectively connected between the antenna 151 and an input of the receiver of the transceiver 153.

As explained herein, the transmitter and receiver of the transceiver 153 exhibit certain power and sensitivity limits based on the components and design of a particular implementation, without the addition of transmit or receive amplifiers 159. One or more transmit amplifiers 159 may be provided to be selectively connected between the output of the transmitter in the antenna to boost the transmit power, such as up to 10 dBm. As another example, the receiver of the transceiver 153 may exhibit a receive sensitivity down to −85 dBm when operated alone without the addition of a separate receive amplifier 159. One or more receive amplifiers 159 may be provided to be selectively connected between the antenna 151 and the input of the receiver of the transceiver 153 to boost the receive sensitivity, such as down to −100 dBm.

As explained herein, the RF circuit 110 is initialized. The transmitter of the transceiver 153 transmits advertisement notices arranged in complexes, followed by sleep states in accordance with an advertisement interval. The receiver of the transceiver 153 performs scan operations, during a receive window, to scan for connection requests. The scan operation, during an individual receive window, may be performed during the same period of time as transmission of the advertisement notices 207 over corresponding advertisement channels. Optionally, the receive window and scan operation may continue after completion of transmission of the advertisement notices. Hence, the scan operation and receive window may temporarily align with the complex of advertisement notices and/or extend beyond the complex of advertisement notices 207 into the sleep state of the advertisement interval.

The RF circuit 110 is configured to handle and/or manage the bi-directional communication link between the IMD 101 and the external instrument (EI) 201. The RF circuit 110 may include communication circuitry configured to transition between a sleep state, a partial awake state, and a fully awake state. For example, when in the fully awake state, the communication circuitry may be configured to execute tasks and actions associated with a communications protocol startup (CPS) instruction set 195 that may include an advertisement scanning related (ASR) instruction subset 205 and a non-ASR instruction subset 206. The communication circuitry, when in the partially awake state, is configured to execute the ASR instruction subset 205. The ASR instruction subset 205 may include transmitting advertising notices 207 over one or more channels according to a wireless communications protocol and scanning the one or more channels for a connection request from an external device. Alternatively, the advertising notices 207 may be stored in the RF circuit 110. Conversely, when a connection request is not received, the communication circuitry may return to the sleep state without performing actions or tasks associated with the non-ASR instruction subset 206 of the CPS instruction set 195. In the example of FIG. 2, the CPS instruction set 195 may be stored in memory 194 and/or 155, which is accessed by the controller circuit 160 and/or processor 157, respectively. The CPS instruction set 195 may provide the wireless protocol syntax for the controller circuit 160 and/or processor 157 to assemble data packets, advertisement notices, connection requests, connection responses, establish communication links 104, and/or partition data received from the EI 201. Additionally or alternatively, the CPS instruction set 195 may be stored in ROM, RAM, firmware or other memory on the RF circuit 110. As a further example, the CPS instruction set 195 may be "stored" through settings of hardware circuitry within the RF circuit 110.

In an embodiment, the communication circuitry of the RF circuit 110, when executing the CPS instruction set 195 with the BLE peripheral application in the fully awake state, may utilize a first amount of power. Also, when executing the ASR instruction subset 205 with the BLE peripheral application in the partially awake state, the CPS instruction set 195 may utilize a second amount of power that is less than the first amount of power. The CPS instruction set 195 may include more task and actions that take a longer period of time and more power to implement versus the task and actions of the ASR instruction subset 205. For example, the second amount of power, to implement the ASR instruction subset, may be between 40%-80% of the first amount of power to implement the entire CPS instruction set. As another example, the second amount of power, to implement the ASR instruction subset, may be between 50%-65% of the first amount of power to implement the entire CPS instruction set.

The RF circuit 110 includes a receiver that scans for connection requests from the EI 201. The RF circuit 110 is controlled by the controller circuit 160 and may support one or more wireless communication protocols while communicating with the EI 201, such as Bluetooth low energy, Bluetooth, Medical Implant Communication Service (MICS), and/or the like. The RF circuit 110 may include a transmitter, receiver, and/or a transceiver. Optionally, the RF circuit 110 may be electrically coupled to an antenna (not shown).

The controller circuit 160 is coupled to the memory 194 by a suitable data/address bus 196, wherein the programmable operating parameters used by the controller circuit 160 are stored and modified, as required, in order to customize the operation of IMD 101 to suit the needs of a particular patient. The memory 194 also stores data sets (raw data, summary data, histograms, etc.), such as the IEGM data, heart sound data, pressure data, Sv02 data and the like for a desired period of time (e.g., 1 hour, 24 hours, 1 month). The memory 194 may store instructions to direct the controller circuit 160 to analyze the cardiac signals and heart sounds identify characteristics of interest and derive values for predetermined statistical parameters.

In addition, the memory 194 stores CPS instruction set 195. The CPS instruction set 195 may be loaded in the memory 194 at the time of manufacture, at the time of activation, at the time of installation or throughout operation. The CPS instruction set 195 includes the ASR instruction subset 205 and non-ASR instruction subset 206. The ASR instruction subset 205 may include at least two of the following: i) expiration of a wake-up timer, ii) processor startup, iii) initialization of a transmit circuit, iv) transmission of advertising data packets, v) scanning one or more channels for a connection request from an external device, or vi) validating or denying an incoming connection request. The non-ASR instruction subset 206 may include at least two of the following: i) initialization of a random-access memory (RAM) segment/block, ii) initialization of an external instrument component, iii) initialization of an operating system service, or iv) initialization of the CPS instruction set 195. In one embodiment, the ASR instruction subset 205 does not include at least two of the following: i) initialization of a random-access memory (RAM) segment/block, ii) initialization of an external instrument component, iii) initialization of an operating system service, or iv) initialization of the CPS instruction set 195. In another embodiment, the ASR instruction subset 205 does not include any of the following: i) initialization of a random-access memory (RAM) segment/block, ii) initialization of an external instrument component, iii) initialization of an operating system service, or iv) initialization of the CPS instruction set 195.

In accordance with embodiments herein, advertisement schedules included in the CPS instruction set 195 balance fast advertisement at low power and low sensitivity in conjunction with slow advertisement at high power and high sensitivity, to afford quick patient initiated communications and to afford longer range automatic connections for remote monitoring. As explained herein, once a connection is made between the external instrument and the IMD, the RF circuit 110 may set the transmit power and receive sensitivity to a desired communications session level (e.g., high) for a duration of the communication session. The transmit power and receive sensitivity are set to the desired communications session level regardless of whether the connection was established using short or long range advertisement, thereby affording a desired communications distance during an active communications session. For example, if a patient wanted to initiate a remote monitoring session, the patient would hold the external instrument (smart phone) close to the body in order to begin the communications session in accordance with short range advertisement. Then once the connection is made, the RF circuit 110 adjusts the transmit power and receive sensitivity to a communications session level (e.g., max power settings), thereby allowing the patient to leave the external instrument (smart phone) on a table and go to bed on the other side of the room without experiencing any disruption of the communication session.

Additionally or alternatively, one or more separate advertisement schedules included in the CPS instruction set 195 may be stored in the memory 194 to be used in connection with individual corresponding EIs 201. For example, when an IMD 101 initially begins communicating with a particular EI 201, the EI 201 may download a corresponding advertisement schedule included in the CPS instruction set 195, along with the instruction to utilize the advertisement schedule included in the CPS instruction set 195 until otherwise instructed. Subsequently, the IMD 101 may communicate with another EI 201 that downloads a corresponding new advertisement schedule included in the CPS instruction set 195, along with an instruction to utilize the new advertisement schedule included in the CPS instruction set 195 until otherwise instructed. As a further example, the IMD 101 may update the advertisement schedule included in the CPS instruction set 195 throughout operation, such as based upon the success rate at which communications links are established, based on delays when establishing communications links and the like.

The operating parameters of the IMD 101 may be non-invasively programmed into the memory 194 through the RF circuit 110 in bi-directional wireless communication with the EI 201. The RF circuit 110 is controlled by the controller circuit 160 and receives data for transmission over a control line 111. The RF circuit 110 allows intra-cardiac electrograms, pressure data, acoustic data, Sv02 data, and status information relating to the operation of IMD 101 (as contained in the controller circuit 160 or memory 194) to be sent to the EI 201 through an established bi-directional communication link 104. The RF circuit 110 also allows the EI 201 to program new parameters and advertisement schedules for the IMD 101.

The RF circuit 110 transmits one or more advertisement notices on one or more advertisement channels. Each advertisement channel is a point to multipoint, unidirectional, channel to carry a repeating pattern of system information messages such as network identification, allowable RF channels to establish the communication link 104, and/or the like that is included within the advertisement notice. The advertisement notice may be repeatedly transmitted after a set duration or an advertisement interval based on an advertisement schedule stored in the memory 194 until the communication link 104 is established with the EI 201.

The IMD 101 may also include a physiologic sensor 112, such as an accelerometer commonly referred to as a "rate-responsive" sensor because it is typically used to record the activity level of the patient according to the exercise state of the patient. Optionally, the physiological sensor 112 may further be used to detect changes in cardiac output, changes in the physiological condition of the heart, or changes in activity (e.g., detecting sleep and wake states) and movement positions of the patient. While shown as being included within IMD 101, it is to be understood that the physiologic sensor 112 may also be external to the IMD 101, yet still be implanted within or carried by the patient. A common type of rate responsive sensor is an activity sensor incorporating an accelerometer or a piezoelectric crystal, which is mounted within the housing 102 of the IMD 101. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient and, in particular, is capable of detecting arousal from sleep or other movement.

The IMD 101 additionally includes a battery 113, which provides operating power to all of the circuits shown. Optionally, the IMD 101 may include an impedance measuring circuit 115 which is enabled by the controller circuit 160 via a control signal 214. Herein, impedance is primarily detected for use in evaluating ventricular end diastolic volume (EDV) but is also used to track respiration cycles. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 115 is advantageously coupled to the switch 174 so that impedance at any desired electrode may be will soon as the obtained.

BLE Peripheral Application in a Fully Awake State and a Partially Awake State

Figure 3A:
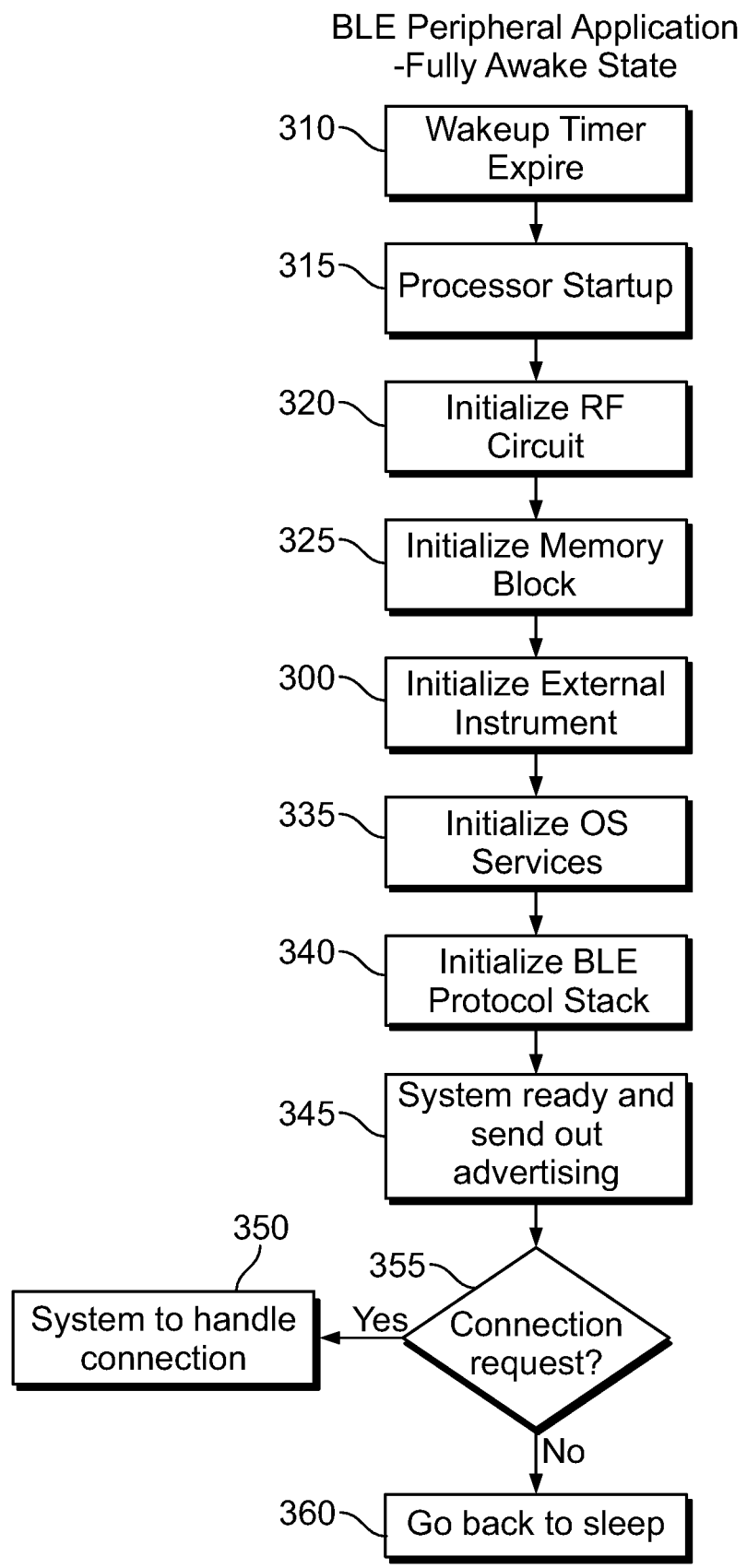
FIG. 3A illustrates an example of initialization blocks of a BLE peripheral application in a fully awake state.

FIG. 3A illustrates an example set of initialization operations/blocks performed by a BLE peripheral application upon entering in a fully awake state. The illustrated process represents a non-limiting example of a set of initialization actions or tasks for a BLE peripheral application operating while communication circuitry of an RF circuit 110 is in a fully awake state.

At 310, the wakeup timer expires and the BLE peripheral application is activated. For example, the IMD 101 may wake up from a predetermined sleep interval. This interval may occur in between connection/advertising events. These connection/advertising events may be controlled by the timing control circuitry 179 as shown in the block diagram in FIG. 2. The timing control circuitry 179 may include a sleep clock. When the wakeup timer expires at the end of the sleep interval, the timing control circuitry 179 may process the current connection/advertising event and establish a new sleep interval using the sleep clock.

At 315, a processor startup routine commences. For example, the startup module 210 may be utilized to control a boot process of the processor. For example, after the timing control circuitry 179 has determined a wakeup interval for the IMD 101, the startup module 210 may include ROM or non-volatile Flash memory with boot code utilized to control the boot process. The ROM may load the boot process. The boot process may include power on, operating system load, and transfer of control to the operating system. For example, subsequent to a power on activity initiated by a user, condition, timer, or other stimulus, a routine may be executed to ensure that the device drivers are functioning properly. Any issues encountered may halt the boot process. Each device in a boot list may load its own routine to ensure proper communication between the devices and the startup module 210. After a successfully completed routine, the operating system 215 may be loaded.

At 320, the RF circuit is initialized. The RF circuit 110 is controlled by the controller circuit 160 and may support one or more wireless communication protocols while communicating with the EI 201, such as BLE, Bluetooth, MICS, and/or the like. The RF circuit 110 may include a transmitter, receiver, and/or a transceiver. The RF circuit 110 transmits one or more advertisement notices on one or more advertisement channels. Each advertisement channel is a point to multipoint, unidirectional, channel to carry a repeating pattern of system information messages such as network identification, allowable RF channels to establish the communication link 104, and/or the like that is included within the advertisement notice. The advertisement notice may be repeatedly transmitted after a set duration or an advertisement interval based on an advertisement schedule stored in the memory 194 until the communication link 104 is established with the EI 201.

At 325, the memory 194 is initialized. For example, operating parameters may be loaded into certain memory locations and/or registers. The memory 194 may store the programmable operating parameters used by the controller circuit 160. The memory 194 also stores data sets, such as the IEGM data, heart sound data, pressure data, Sv02 data and the like for a desired period of time. The memory 194 may also store instructions to direct the controller circuit 160 to analyze the cardiac signals and heart sounds identify characteristics of interest and derive values for predetermined statistical parameters. Additionally, the memory 194 stores one or more advertisement schedules included in the CPS instruction set 195.

At 330, external instrument initialization is performed. For example, the application on an external instrument, such as a programming or mobile device, is activated by a user for an interactive session or by a pre-scheduled wake up timer for background communications to the IMD for an IMD status check. Once the communication session is started by either means, the EI 201 sends a connection request. The connection request may include a unique ID for the external instrument. The unique ID may be loaded into a register of the RF circuit 110 during the initialization at 330.

At 335, operating system services are initialized. After a successful completed BIOS, the operating system 215 may commence to run applications. The operating system 215 may comprise various application programs for collecting and analyzing biological signals.

At 340, the BLE protocol stack 220 is initialized. The protocol stack 220 may include a host and controller comprising multiple layers utilized for communication.

At 345, the BLE peripheral application transmits one or more advertising notices. The protocol stack 220 controls the time at which the advertising notice(s) are sent. The Link Layer (LL) of the controller of the protocol stack 220 controls the radiofrequency (RF) state of the device, which includes the advertising state. It should be noted that the scan request and scan response activities occur during the advertising intervals of both applications.

At 355, the BLE peripheral application determines whether a connection request has been received. If there are no connection requests, the process ends for both applications and the IMD goes back to sleep as illustrated at 360. Alternatively, if a connection request is received, the process proceeds to 350.

At 350, the BLE peripheral application analyzes the content of the connection request, such as to determine if the connection request was sent by an authorized EI 201. If the connection request is sent by an authorized EI 201, the IMD 101 and EI 201 exchange additional information to initiate a communications session. The EI 201 and IMD 101 connect, and the EI 201 is allowed to access the information gathered by the IMD 101, such as intra-cardiac electrograms, pressure data, acoustic data, Sv02 data, and status information relating to the operation of IMD 101. At this point in the process, the IMD 101 is fully awake.

Figure 3B:
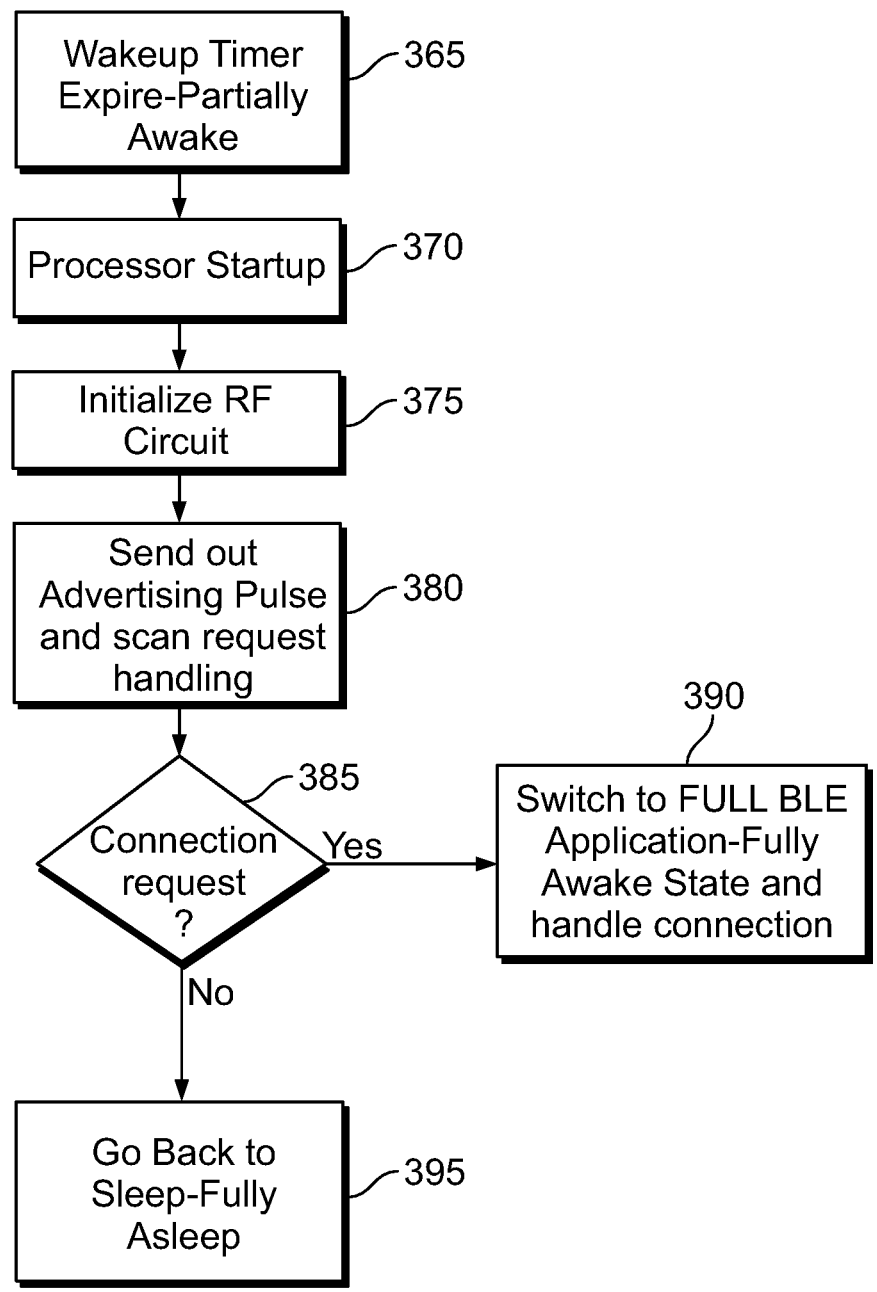
FIG. 3B illustrates an example of initialization blocks of a BLE advertising application in a partially awake state.

FIG. 3B illustrates an example of initialization operations/blocks of a BLE peripheral application while in a partially awake state. The BLE peripheral application operates in a partially awake state until full power is required and is shown from a firmware perspective that interacts with the Bluetooth Low Energy system on a chip (SoC).

At 365, the wakeup timer expires and activates a partially wake (low power) BLE application. For example, in either application the IMD 101 may wake up from a predetermined sleep interval. This interval may occur in between connection/advertising events. These connection/advertising events may be controlled by the timing control circuitry 179 as shown in the block diagram in FIG. 2. The timing control circuitry 179 may include a sleep clock. When the wakeup timer expires at the end of the sleep interval, the timing control circuitry 179 may process the current connection/advertising event and establish a new sleep interval using the sleep clock. At this point in the process, the IMD 101 is partially awake.

At 370, the processor startup routine is implemented similar to the routine described in connection with the operations at 310. At 375, the RF circuit is initialized similar to the routine described in connection with the operations at 315.

The low power BLE application skips the steps from 325 through 340 as shown in the BLE peripheral application in a fully awake state. The low power BLE application does not initialize the memory block, the external instrument, the OS service, or the BLE protocol stack during this portion of the process. This change in process shortens the time necessary for the processor and hardware blocks to be active during each advertising opportunity, conserving energy.

At 380, the BLE peripheral application sends one or more advertising notices. At 385, the BLE peripheral application determines whether a connection request was received. If no connection request is received, the process ends and the IMD goes back to sleep as illustrated at 395. Alternatively, if a connection request is received, the process proceeds to 390. At 390, the BLE peripheral application analyzes the connection request and initiates a communications session if appropriate. At this point in the process, the IMD 101 is in the fully awake state.

Figure 4:
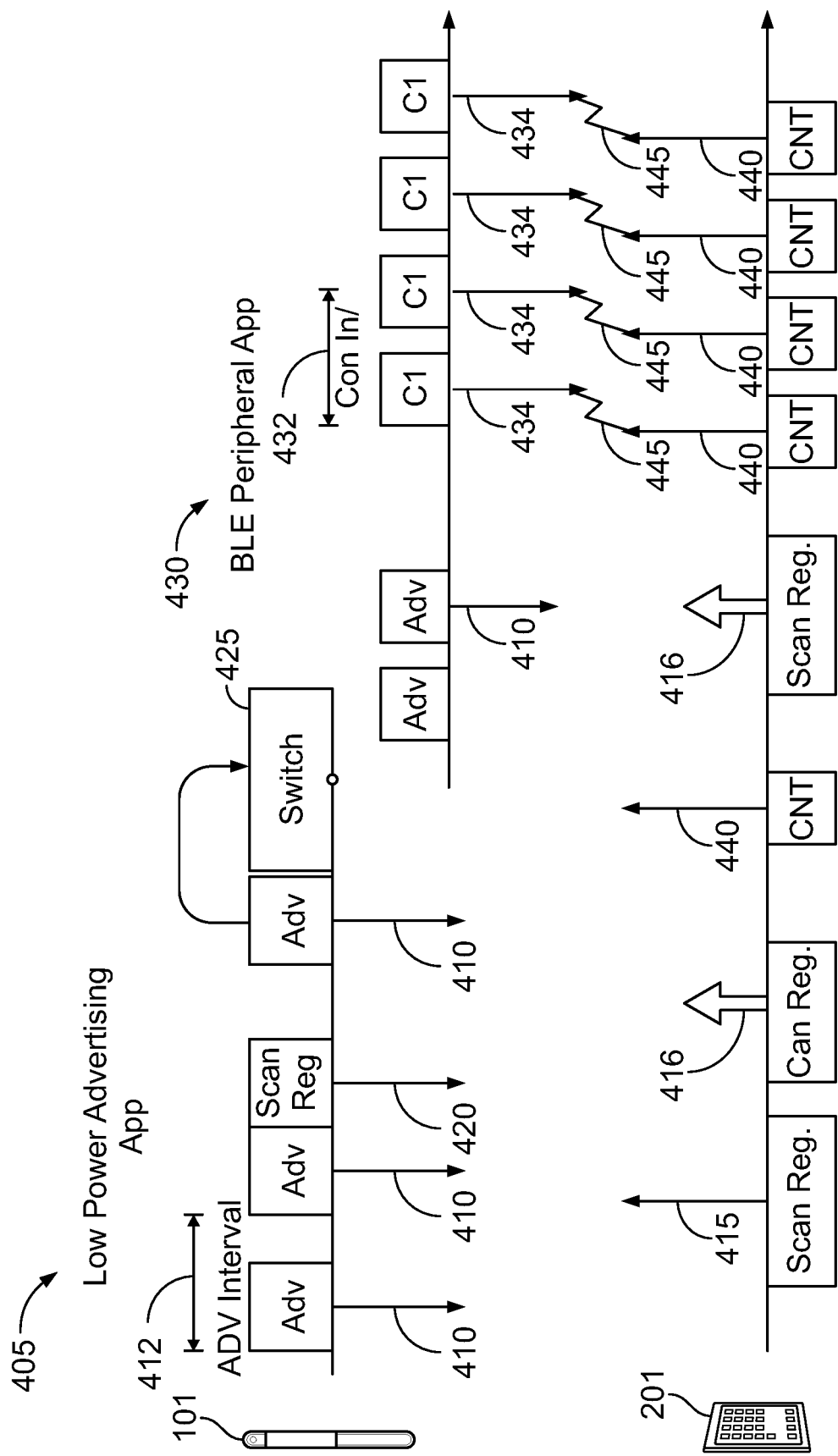
FIG. 4 illustrates an example of an application switch sequence between a BLE advertising application in a partially awake state and a BLE advertising application in a fully awake state in accordance with embodiments herein.

FIG. 4 illustrates an example of an application switching sequence between a Low Power (partially awake) Advertising Application and a (fully awake) BLE peripheral Firmware Application. The IMD 101 transmits advertising notices 410 at advertising interval 412 during different advertising periods while in the partially awake state. The EI 201 transmits a scan request 415 to request a connection to the IMD 101. Once the scan request 415 is received by the IMD 101, a scan response 420 may be sent to the EI 201. If the scan response 420 indicates that the EI 201 is approved for a connection 440 to the IMD 101 and subsequent communication 445, a switching operation 425 is initiated and the partially awake advertising application 405 switches to the fully awake advertising 430 when a connection request 435 is received. The partially awake advertising application 405 hands the process over to the fully awake advertising application 430. The scan request 415 may be processed by analyzing identifying features of the EI 201.

When the fully awake advertising application 430 takes control, the memory block 194 is initialized (action/task 325 in FIG. 3A) in the fully awake advertising application. For example, program instructions and/or parameters may be loaded into RAM, registers or other memory locations. Various indices into the memory are initialized. In addition, an external instrument is initialized (action/task 330). In addition, the operating system services are initialized (action/task 335) and the BLE protocol stack 220 is initialized (action/task 340). Thereafter, a communications session is established.

Figure 5:
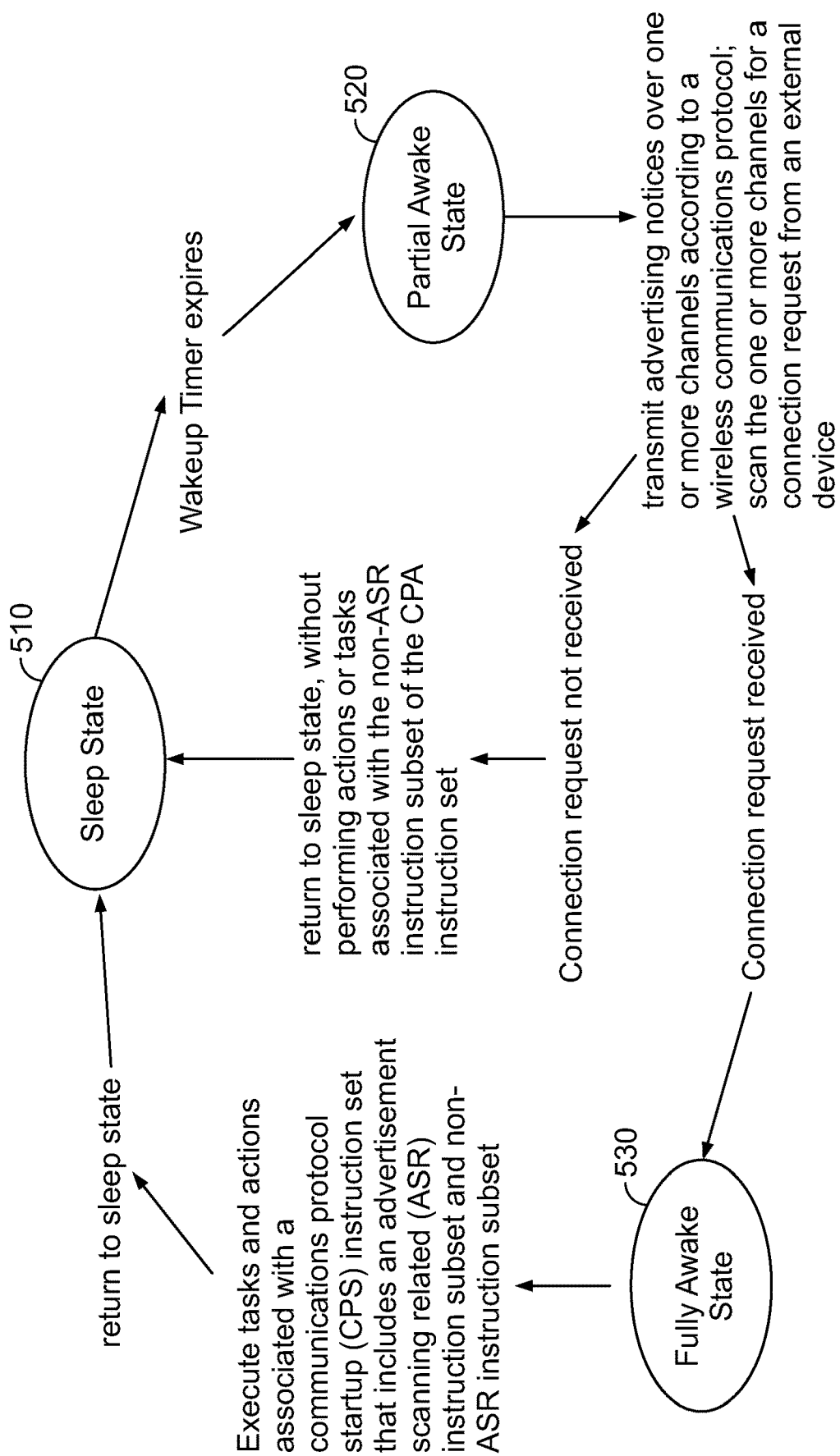
FIG. 5 is a state machine diagram illustrating states of communication circuitry configured in accordance with embodiments herein.

FIG. 5 is a state machine diagram illustrating states of a communication circuitry of an IMD 101, configured in accordance with an embodiment herein. Initially, the communication circuitry begins in a sleep state 510. The communication circuitry remains in the sleep state until a wakeup timer expires. Once the wakeup timer expires, the communication circuitry transitions from the sleep state to a partially awake state 520, which also may be referred to as a low power advertising state. During the partially awake state, the communication circuitry is configured to transmit advertising notices over one or more channels according to a wireless communications protocol and scan the one or more channels for a connection request from an external device.

If a connection request is received from an external device, the connection circuitry may be configured to transition to a fully awake state 530. The fully awake state may also be considered a full power advertising state. During the fully awake state, the communication circuitry is configured to execute tasks and actions associated with a communications protocol startup (CPS) instruction set that includes an advertisement scanning related (ASR) instruction subset and a non-ASR instruction subset. After completing the required handling duties, the communication circuitry may return to the sleep state until the next wakeup timer expires.

If, however, a connection request is not received, the communication circuitry may return to sleep state, without performing actions or tasks associated with the non-ASR instruction subset of the CPA instruction set.

Further, when the communication circuitry executes the CPA instruction set while in the fully awake state, utilizes a first amount of power. When executing the ASR instruction subset while in the partially awake state, the communication circuitry utilizes a second amount of power that is less than the first amount of power. The complete CPS instruction set includes more task and actions that take a longer period of time and more power to implement versus the limited set of task and actions of the ASR instruction subset.

Additionally or alternatively, the communication circuitry may include hardware or firmware, in which case the ASR instruction subset may include at least two of the following: i) expiration of a wake-up timer, ii) processor startup, iii) initialization of a transmit circuit, iv) transmission of advertising data packets, v) scanning one or more channels for a connection request from an external device, or vi) validating or denying an incoming connection request. The ASR instruction subset may not include non-ASR instruction subset.

Moreover, the communication circuitry may include hardware or firmware, and the non-ASR instruction subset may include at least two of the following: i) initialization of a random-access memory (RAM) segment/block, ii) initialization of an external instrument component, iii) initialization of an operating system service, or iv) initialization of a communications protocol stack.

CLOSING

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. The program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A system, comprising:
an external device; and
a medical device configured to communicate with the external device wherein the medical device comprises a communication circuitry having a first power state and a second power state, wherein the communication circuitry is configured to transition from the first power state to the second power state at an interval, wherein the second power state uses more power than the first power state;
wherein, when the communication circuitry is in the second power state, the communication circuitry is configured to transmit advertising notices according to an advertising notice schedule,
wherein, when a request is not received from the external device in response to the advertising notices, the medical device transitions to the first power state,
wherein, when a request is received from the external device, the medical device establishes a bi-directional communication link with the external device, and
wherein the medical device transitions to a third power state after receiving the request from the external device, wherein the third power state uses more power than the second power state.

2. The system of claim 1, wherein when the communication circuitry is in the second power state, the communication circuitry is further configured to scan one or more channels for a connection request from the external device.

3. The system of claim 1, wherein the medical device comprises a sensing circuit configured to collect sensed physiological data.

4. The system of claim 1, further comprising a sensor for continuously monitoring a body generated analyte.

5. The system of claim 1, wherein the medical device further comprises an accelerometer for determining an activity level of the user.

6. The system of claim 1, wherein the medical device represents at least one of a neurostimulator device, implantable leadless monitoring device, implantable leadless therapy device, body generated analyte test device, pacemaker, cardioverter, cardiac rhythm management device, or defibrillator.

7. The system of claim 1, wherein the first, second and third power states correspond to a sleep state, a partial awake state and a fully awake state, respectively.

8. The system of claim 1, wherein the communication circuitry is configured to execute a first instruction subset associated transmitting the advertising notices and a second instruction subset not associated with transmitting the advertising notices;
when in the second power state, the communication circuitry configured to execute the first instruction subset and when a connection request is not received, return to the first power state, without performing actions or tasks associated with the second instruction subset.

9. The system of claim 1, wherein,
when in the second power state, the communication circuitry is configured to:
i) transmit advertising notices over one or more channels according to a wireless communications protocol; and
ii) scan the one or more channels for a connection request from an external device; and
when in the second power state, the communication circuitry is configured to not perform at least two of:
i) initialization of a random-access memory (RAM) segment/block,
ii) initialization of an external instrument component,
iii) initialization of an operating system service, or
iv) initialization of a communications protocol stack.

10. A computer implemented method, comprising:
under control of one or more processors of a medical device, where the one or more processors are configured with specific executable instructions for,
collecting biological signals;
implementing program instructions to at least one of analyze the biological signals, manage storage of the biological signals or deliver a therapy;
operating the medical device in first and second power states as follows:

transitioning the medical device from the first power state to the second power state at an interval, wherein the second power state uses more power than the first power state;

when in the second power state, transmitting advertising notices according to an advertising notice schedule, when a request is not received from an external device in response to the advertising notices, transitions to the first power state, when a request is received from the external device in response to the advertising notices, establishing a bi-directional communication link with the external device, and transitioning to a third power state after receiving the request from the external device, wherein the third power state uses more power than the second power state.

11. The method of claim 10, wherein, when in the second power state, scanning one or more channels for a connection request from the external device.

12. The method of claim 10, further comprising monitoring a body generated analyte.

13. The method of claim 10, further comprising utilizing an accelerometer for determining an activity level of the user.

14. The method of claim 10, wherein the medical device represents at least one of a neurostimulator device, implantable leadless monitoring device, implantable leadless therapy device, body generated analyte test device, pacemaker, cardioverter, cardiac rhythm management device, or defibrillator.

15. The method of claim 10, wherein the first, second and third power states correspond to a sleep state, a partial awake state and a fully awake state, respectively.

16. The method of claim 15, wherein, when in the partially awake state, the communication circuitry is configured to not perform at least two of:
  i) initialization of a random-access memory (RAM) segment/block,
  ii) initialization of an external instrument component,
  iii) initialization of an operating system service, or
  iv) initialization of a communications protocol stack.

17. The method of claim 10, wherein, when in the second power state, the advertising notices transmitted without performing initialization actions or tasks associated with at least three of:
  i) initialization of a random-access memory (RAM) segment/block,
  ii) initialization of an external instrument component,
  iii) initialization of an operating system service, or
  iv) initialization of a communications protocol stack.

18. The method of claim 10, wherein,
when in the second power state, the communication circuitry is configured to:
  transmit advertising notices over one or more channels according to a wireless communications protocol; and
  scan the one or more channels for a connection request from an external.

* * * * *